US010010455B2

(12) United States Patent
Schoultz et al.

(10) Patent No.: US 10,010,455 B2
(45) Date of Patent: Jul. 3, 2018

(54) BONDING AND SLITTING DEVICE

(71) Applicant: KIMBERLY-CLARK WORLDWIDE, INC., Neenah, WI (US)

(72) Inventors: Adam Schoultz, Mason, OH (US); Joseph J. Sina, Appleton, WI (US); Marcille Faye Ruman, Oshkosh, WI (US); Kathy Irene Bennett, Neenah, WI (US); Joseph Daniel Coenen, Kaukauna, WI (US); Daniel Marvin Nussbaum, Neenah, WI (US); Lori Roocks, Menasha, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 15/076,780

(22) Filed: Mar. 22, 2016

(65) Prior Publication Data
US 2016/0199233 A1 Jul. 14, 2016

Related U.S. Application Data

(62) Division of application No. 14/091,829, filed on Nov. 27, 2013, now Pat. No. 9,320,655.

(51) Int. Cl.
*A61F 13/15* (2006.01)
*B29C 65/08* (2006.01)
(Continued)

(52) U.S. Cl.
CPC .. *A61F 13/15739* (2013.01); *A61F 13/15699* (2013.01); *A61F 13/15747* (2013.01);
(Continued)

(58) Field of Classification Search
CPC .......... A61F 13/15757; A61F 13/15699; A61F 13/00; A61F 13/10; A61F 13/15;
(Continued)

(56) References Cited

U.S. PATENT DOCUMENTS

| 1,397,579 A | 11/1921 | Guinzburg |
| 4,100,324 A | 7/1978 | Anderson et al. |

(Continued)

FOREIGN PATENT DOCUMENTS

| EP | 0459178 | 12/1991 |
| EP | 0217032 | 2/1992 |

(Continued)

OTHER PUBLICATIONS

Notification of Transmittal of the International Search Report and the Written Opinion of the International Searching Authority for International Application No. PCT/IB2014/065883, dated Feb. 13, 2015; 10 pages.

*Primary Examiner* — Jacob T Minskey
*Assistant Examiner* — Matthew Hoover
(74) *Attorney, Agent, or Firm* — Armstrong Teasdale LLP

(57) ABSTRACT

A bonding and slitting device is adapted to form fin seams in absorbent articles having a front waist region, a back waist region, and a crotch region extending between the front waist region and the back waist region. The device includes a first bonding member and a second bonding member having a contact element configured to cooperate with the first bonding member to bond the front region of the chassis to the back region to define the fin seams. A slitter is configured to simultaneously act on material outboard of the bonds from both the front and back regions of the chassis.

17 Claims, 9 Drawing Sheets

(51) Int. Cl.
*B29C 65/74* (2006.01)
*B29C 65/00* (2006.01)
*A61F 13/496* (2006.01)
*B29L 31/48* (2006.01)

(52) U.S. Cl.
CPC ........ *B29C 65/087* (2013.01); *B29C 65/7435* (2013.01); *B29C 65/7443* (2013.01); *B29C 66/1122* (2013.01); *B29C 66/21* (2013.01); *B29C 66/431* (2013.01); *B29C 66/7294* (2013.01); *B29C 66/72343* (2013.01); *B29C 66/81433* (2013.01); *B29C 66/83413* (2013.01); *B29C 66/8432* (2013.01); *A61F 13/4963* (2013.01); *A61F 2013/15869* (2013.01); *B29C 66/71* (2013.01); *B29L 2031/4878* (2013.01); *Y10T 156/1051* (2015.01); *Y10T 156/1313* (2015.01)

(58) Field of Classification Search
CPC ...... A61F 13/15; A61F 13/156; A61F 13/156; A61F 13/1569; A61F 13/1569
See application file for complete search history.

(56) References Cited

U.S. PATENT DOCUMENTS

| | | |
|---|---|---|
| 4,205,679 A | 6/1980 | Repke et al. |
| 4,573,986 A | 3/1986 | Minetola et al. |
| 4,597,760 A | 7/1986 | Buell |
| 4,610,681 A | 9/1986 | Strohbeen et al. |
| 4,630,320 A * | 12/1986 | Van Gompel .......... A41B 9/001 2/183 |
| 4,663,220 A | 5/1987 | Wisneski et al. |
| 4,699,621 A | 10/1987 | Stevens et al. |
| 4,701,172 A | 10/1987 | Stevens |
| 4,747,846 A | 5/1988 | Boland et al. |
| 4,846,825 A | 7/1989 | Enloe et al. |
| 4,940,464 A | 7/1990 | Van Gompel et al. |
| 5,046,272 A | 9/1991 | Vogt et al. |
| 5,064,421 A | 11/1991 | Tracy |
| 5,104,116 A | 4/1992 | Pohjola |
| 5,224,405 A | 7/1993 | Pohjola |
| 5,226,992 A | 7/1993 | Morman |
| 5,236,430 A * | 8/1993 | Bridges ............. A61F 13/49012 2/400 |
| 5,284,703 A | 2/1994 | Everhart et al. |
| 5,350,624 A | 9/1994 | Georger et al. |
| 5,385,775 A | 1/1995 | Wright |
| 5,476,458 A | 12/1995 | Glaug et al. |
| 5,482,765 A | 1/1996 | Bradley et al. |
| 5,486,166 A | 1/1996 | Bishop et al. |
| 5,490,846 A | 2/1996 | Ellis et al. |
| 5,492,751 A | 2/1996 | Butt, Sr. et al. |
| 5,496,429 A | 3/1996 | Hasse et al. |
| 5,593,401 A | 1/1997 | Sosalla et al. |
| 5,601,544 A * | 2/1997 | Glaug ................. A61F 13/4942 604/373 |
| 5,607,416 A | 3/1997 | Yamamoto et al. |
| 5,624,420 A | 4/1997 | Bridges et al. |
| 5,624,424 A | 4/1997 | Sausaka et al. |
| 5,662,638 A | 9/1997 | Johnson et al. |
| 5,706,524 A | 1/1998 | Herrin et al. |
| 5,714,156 A | 2/1998 | Schmidt et al. |
| 5,766,389 A | 6/1998 | Brandon et al. |
| 5,772,825 A | 6/1998 | Schmitz |
| 5,779,831 A | 7/1998 | Schmitz |
| 5,820,973 A | 10/1998 | Dodge, II et al. |
| 5,870,778 A | 2/1999 | Tharpe et al. |
| 5,885,266 A | 3/1999 | Chihani et al. |
| 6,057,024 A | 5/2000 | Mleziva et al. |
| 6,113,717 A | 9/2000 | Vogt et al. |
| 6,369,291 B1 | 4/2002 | Uchimoto et al. |
| 6,380,292 B1 | 4/2002 | Gibes et al. |
| 6,383,170 B1 | 5/2002 | Mishima et al. |
| 6,394,991 B1 | 5/2002 | Takei et al. |
| 6,531,015 B1 * | 3/2003 | Gardner, Jr. ....... A61F 13/15593 156/179 |
| 6,552,245 B1 | 4/2003 | Roessler |
| 6,562,017 B1 | 5/2003 | Nakaoka et al. |
| 6,576,809 B1 | 6/2003 | Inoue et al. |
| 6,585,840 B2 | 7/2003 | Rabe et al. |
| 6,605,071 B1 | 8/2003 | Gray et al. |
| 6,605,173 B2 | 8/2003 | Glaug et al. |
| 6,645,190 B1 | 11/2003 | Olson et al. |
| 6,753,455 B2 | 6/2004 | Chmielewski |
| 6,822,136 B1 | 11/2004 | Niemeyer et al. |
| 6,899,780 B2 | 5/2005 | Rajala et al. |
| 6,916,750 B2 | 7/2005 | Thomas et al. |
| 6,939,335 B2 | 9/2005 | Franke et al. |
| 6,962,578 B1 | 11/2005 | Lavon et al. |
| 6,969,378 B1 | 11/2005 | Vukos et al. |
| 6,969,441 B2 | 11/2005 | Welch et al. |
| 7,014,632 B2 | 3/2006 | Takino et al. |
| 7,047,572 B2 | 5/2006 | Hopkins |
| 7,227,051 B2 | 6/2007 | Mitsui et al. |
| 7,264,686 B2 | 9/2007 | Thorson et al. |
| 7,666,175 B2 | 2/2010 | Trennepohl |
| 7,727,217 B2 | 6/2010 | Hancock-Cooke |
| 7,777,094 B2 | 8/2010 | Mori et al. |
| 7,794,441 B2 | 9/2010 | Ashton et al. |
| 7,803,244 B2 | 9/2010 | Siquiera et al. |
| 7,854,022 B2 | 12/2010 | Warren et al. |
| 7,901,390 B1 | 3/2011 | Ashton et al. |
| 8,109,916 B2 | 2/2012 | Wennerback |
| 8,168,028 B2 | 5/2012 | Schneider et al. |
| 8,212,102 B2 | 7/2012 | Kumasaka |
| 8,282,616 B2 | 10/2012 | Lehto et al. |
| 8,361,913 B2 | 1/2013 | Siquiera |
| 2002/0092604 A1 | 7/2002 | McCabe et al. |
| 2003/0000620 A1 | 1/2003 | Herrin et al. |
| 2004/0064125 A1 | 4/2004 | Justmann et al. |
| 2004/0102757 A1 | 5/2004 | Olson |
| 2006/0149208 A1 | 7/2006 | Carr |
| 2006/0247591 A1 | 11/2006 | Hughes et al. |
| 2007/0073262 A1 | 3/2007 | Babusik et al. |
| 2007/0208318 A1 | 9/2007 | Loritz et al. |
| 2008/0134487 A1 | 6/2008 | Harlono |
| 2008/0287897 A1 | 11/2008 | Guzman Reyes et al. |
| 2009/0157034 A1 | 6/2009 | Mattingly et al. |
| 2009/0178755 A1 | 7/2009 | Hornung et al. |
| 2010/0049155 A1 | 2/2010 | Soderbergh et al. |
| 2010/0063468 A1 | 3/2010 | Lehto et al. |
| 2010/0076390 A1 | 3/2010 | Norrby et al. |
| 2011/0092941 A1 | 4/2011 | Ruman et al. |
| 2011/0125122 A1 * | 5/2011 | Thorson ............ A61F 13/15593 604/385.3 |
| 2012/0244078 A1 | 9/2012 | Schlinz et al. |
| 2012/0316523 A1 | 12/2012 | Hippe et al. |

FOREIGN PATENT DOCUMENTS

| | | |
|---|---|---|
| EP | 0638304 | 3/1999 |
| EP | 0941727 | 9/1999 |
| EP | 0955976 | 3/2002 |
| EP | 2022453 | 2/2009 |
| GB | 2250921 | 6/1992 |
| JP | 2007195792 | 8/2007 |
| WO | 0037009 | 6/2000 |
| WO | 0188245 | 11/2001 |

\* cited by examiner

BONDING AND SLITTING DEVICE

CROSS REFERENCE TO RELATED APPLICATION

This application is a divisional application of U.S. patent application Ser. No. 14/091,829 entitled METHOD OF MANUFACTURING AN ABSORBENT ARTICLE HAVING A FIN SEAM, filed Nov. 27, 2013, the disclosure of which is fully incorporated herein by reference.

FIELD

The present invention relates generally to methods of manufacturing absorbent articles, and more particularly to methods of manufacturing absorbent articles having fin seams.

BACKGROUND

Exemplary absorbent articles include training pants, diapers, incontinence products, disposable underwear, medical garments, absorbent swim wear, and the like. Training pants (albeit, not exclusively) are disposable absorbent articles configured for use in the toilet training process. Toilet training is a process that includes many training techniques and aids that can be used by parents or other caregivers. One aspect of the total toilet training process is changing from the use of diapers to the use of training pants to help the child understand that he or she should now use the toilet.

Many caregivers underestimate the difficulty of teaching the toilet training process to young children. If a child does not respond to an initial toilet training instruction or introduction, the caregiver can be at a loss for finding techniques, methods, or teaching tools to encourage the child to master the art of toilet training. Thus, while various teaching tools such as books, videotapes, charts with stickers, personalized toilets, and interactive toilet training kits are available, there remains a need for improved motivational mechanisms to facilitate the toilet training process.

One motivational mechanism is the use of training pants having an improved aesthetic appearance. Specifically, a child is encouraged to wear a garment that resembles underwear worn by older children. Thus, there is an ongoing need to increase the appeal of the toilet training process to children, and to improve the aesthetic appearance of training pants. However, it is important that any modifications to the training pants to meet these needs do not compromise the use of the articles or any functional features of the articles (e.g., wetness indicators, absorbency, leakage protection, etc.).

Accordingly, there is a need for a training pant having an aesthetic appearance similar to conventional underwear.

SUMMARY

In one aspect, a method for manufacturing absorbent articles is disclosed. Each of the absorbent articles comprises a chassis and an absorbent structure disposed on the chassis. The chassis has a front waist region, a back waist region, and a crotch region extending between the front waist region and the back waist region. The method generally comprises folding each of the absorbent articles about a fold line generally bisecting the article such that the front and back waist regions are positioned in facing relationship, and simultaneously bonding and one of trimming and weakening the front and back waist regions adjacent each opposing side edge of the article to form a pair of fin seams.

In another aspect, a method for manufacturing absorbent articles is disclosed. Each of the absorbent articles comprises a chassis and an absorbent structure disposed on the chassis. The chassis has a front waist region, a back waist region, and a crotch region extending between the front waist region and the back waist region. The chassis defines a waist opening and a pair of leg openings. A waist elastic member is adapted to extend around at least a portion of the waist opening and a pair of leg elastic members is adapted to extend around at least a portion of respective ones of the pair of leg openings. The method generally comprises folding each of the absorbent articles about a fold line generally bisecting the article such that the front and back waist regions are positioned in facing relationship, and simultaneously bonding and one of trimming and weakening the front and back waist regions adjacent each opposing side edge of the article to form a pair of fin seams such that at least a portion of one of the waist elastic member and the leg elastic members defines part of each of the fin seams.

In yet another aspect, a bonding and slitting device is adapted to form fin seams in absorbent articles. The absorbent articles have a front waist region, a back waist region, and a crotch region extending between the front waist region and the back waist region. The device generally comprises a first bonding member and a second bonding member having a contact element configured to cooperate with the first bonding member to bond the front region of the chassis to the back region to define the fin seams and a slitter configured to simultaneously act on material outboard of the bonds from both the front and back regions of the chassis.

Other features of the invention will be in part apparent and in part pointed out hereinafter.

DETAILED DESCRIPTION

Figure 1:
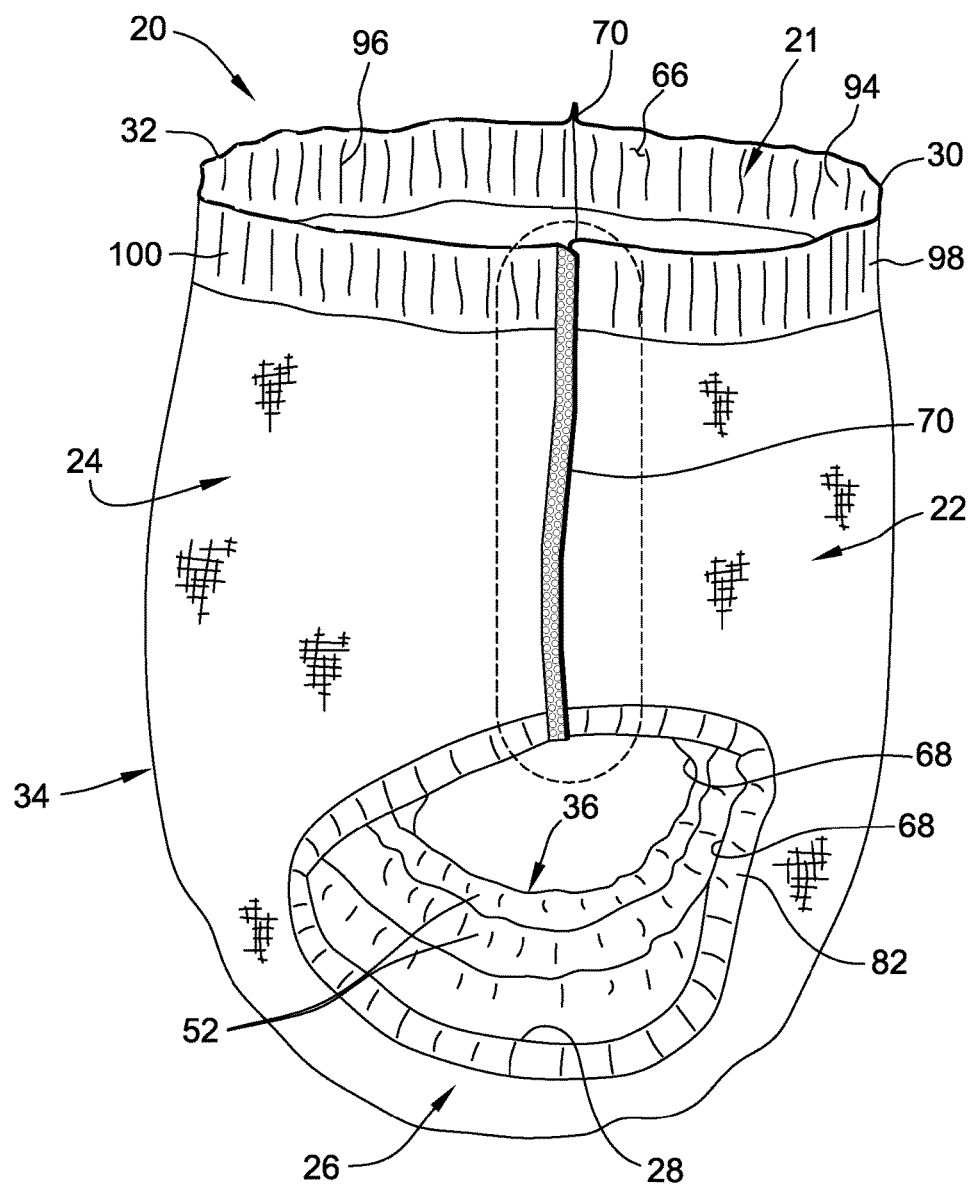
FIG. 1 is a side perspective of one suitable embodiment of an absorbent article shown in the form of a training pant, the training pant having bonded fin seams formed along the sides of the training pant.

Referring now to the drawings and in particular to FIG. 1, one suitable embodiment of an absorbent article is illustrated in the form of a child's toilet training pant and is indicated in its entirety by the reference numeral 20. The term absorbent article generally refers to articles that may be placed against or in proximity to a body of a wearer to absorb and/or retain various exudates from the body. The absorbent training pant 20 may or may not be disposable. Disposable refers to articles that are intended to be discarded after a limited period of use instead of being laundered or otherwise conditioned for reuse. It is understood that the embodiments of the present disclosure are suitable for use with various other absorbent articles intended for personal wear, including but not limited to diapers, swim diapers, feminine hygiene products (e.g., sanitary napkins), incontinence products, medical garments, surgical pads and bandages, other personal care or health care garments, and the like without departing from the scope of the present disclosure.

By way of illustration only, various materials and methods for constructing training pant such as the pant 20 of the present disclosure are disclosed in U.S. patent application Ser. No. 14/062,278 filed Oct. 24, 2013 by Ruman et al.; U.S. patent application Ser. No. 14/068,918 filed Oct. 31, 2013 by Sina et al.; U.S. patent application Ser. No. 14/068,913 filed Oct. 31, 2013 by Bennett et al.; PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al., which are incorporated herein by reference.

Figure 2:
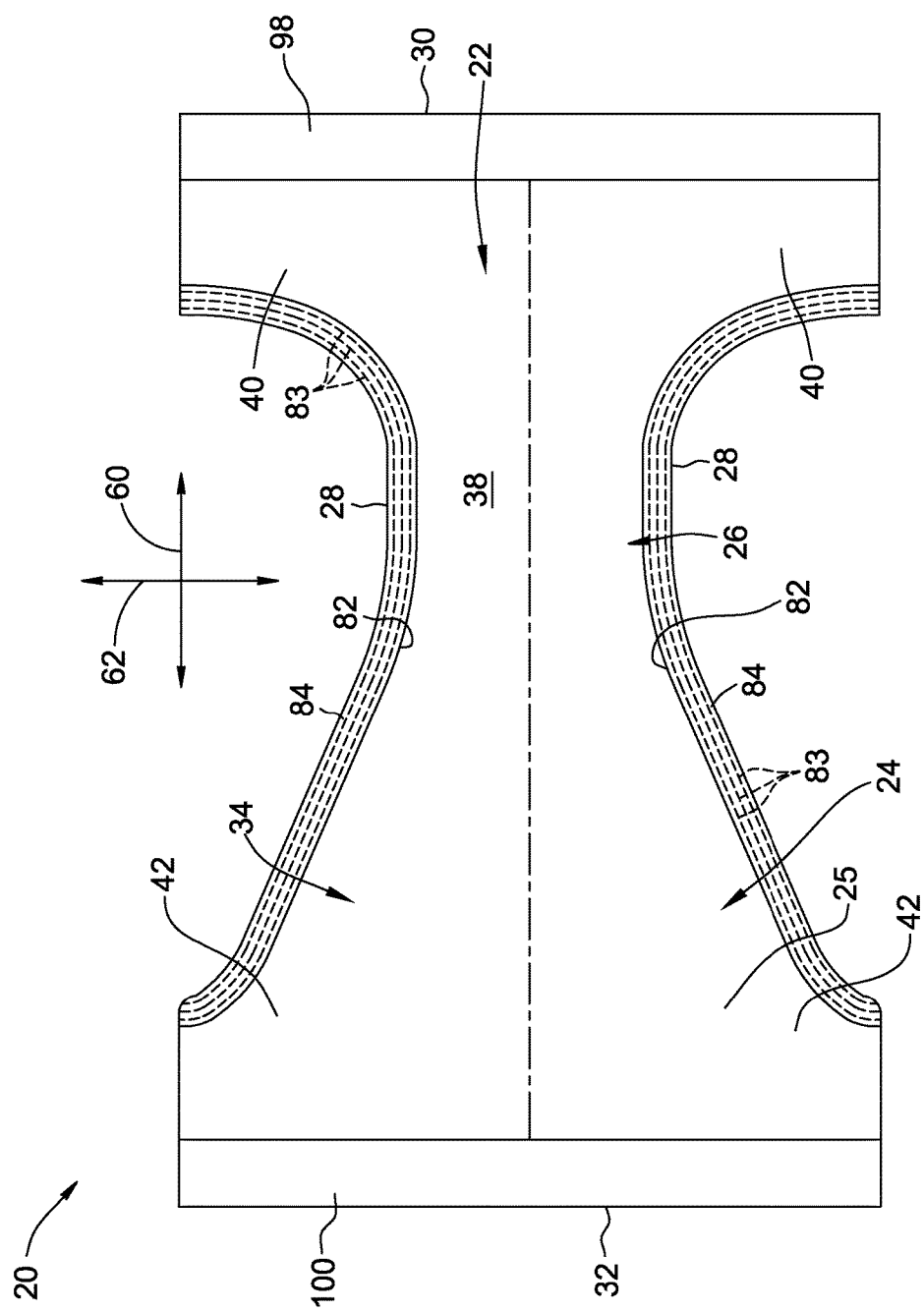
FIG. 2 is a bottom plan view of the training pant of FIG. 1 with the training pant in an unbonded, unfolded and laid flat condition, and showing a surface of the training pant adapted to face away from the wearer during use.
Figure 3:
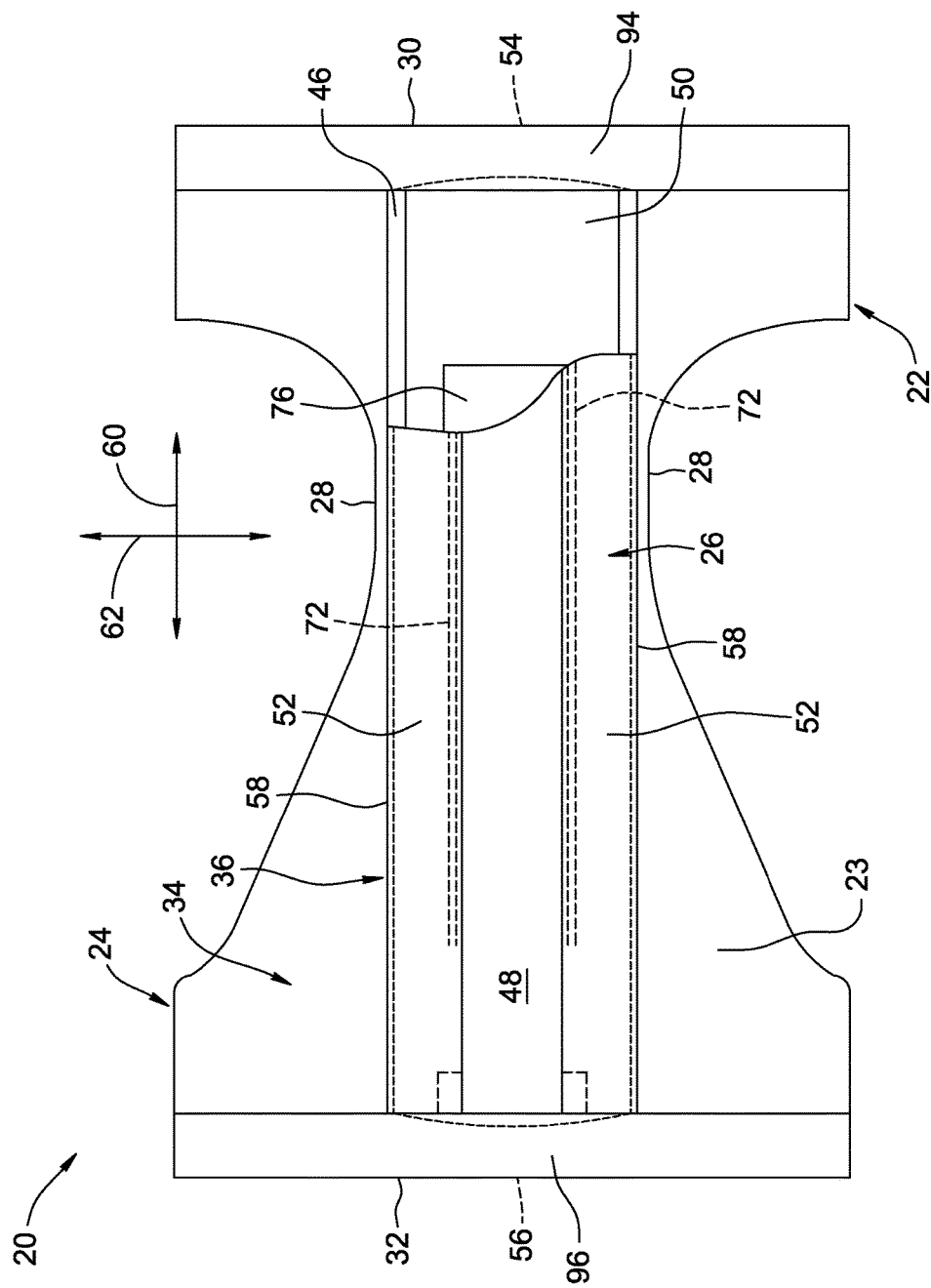
FIG. 3 is a top plan view similar to FIG. 2 but showing a surface of the training pant adapted to face the wearer during use, portions of the training pant being cut away to show underlying features.

As seen in FIGS. 1-3, the training pant 20 has a front waist region 22, a back waist region 24, and a crotch region 26 disposed longitudinally between and interconnecting the front and back waist regions. The front waist region 22, the back waist region 24 and the crotch region 26 are indicated generally by the respective reference numbers. The training pant 20 also has a pair of laterally opposite side edges 28 and a pair of longitudinally opposite waist edges, respectively designated front waist edge 30 and back waist edge 32. The front waist region 22 is contiguous with the front waist edge 30, and the back waist region 24 is contiguous with the back waist edge 32.

With reference to FIGS. 2 and 3, the training pant 20 includes a chassis, indicated generally at 34, and an absorbent assembly, indicated generally at 36, attached to the chassis 34. Arrows 60 and 62 in FIGS. 2 and 3 depict the orientation of a longitudinal axis and a transverse or lateral axis, respectively, of the training pant 20. The illustrated absorbent assembly 36 extends longitudinally from the front waist region 22 through the crotch region 26 to the back waist region 24. While the illustrated absorbent assembly 36 is shown and described herein as extending from the crotch region 26 into both the front and back waist regions 22 and 24, it is contemplated that the absorbent assembly 36 may extend from the crotch region 26 into primarily the front waist region 22, or into primarily the back waist region 24, without departing from some aspects of this disclosure. Further, the absorbent assembly 36 may extend any suitable length along the crotch region 26 and/or into the front waist region 22 and/or the back waist region 24. In the illustrated embodiment, the chassis 34 and the absorbent assembly 36 are formed separately from one another. It is contemplated, however, that the chassis 34 and the absorbent assembly 36 may be integrally formed with one another in some embodiments. It is further contemplated that in some suitable embodiments the absorbent assembly 36 can be disposable and the chassis 34 can be non-disposable.

As seen in FIG. 2, the chassis 34 includes a longitudinally extending central portion 38, a pair of laterally opposite front side portions 40 extending outward from the central portion 38 at the front waist region 22 (thereby forming transversely outer portions of the front waist region, and more broadly in part forming transversely opposite sides of the training pant), and a pair of laterally opposite back side portions 42 extending outward from the central portion at the back waist region 24 (thereby forming transversely outer portions of the back waist region, and together with the front side portions 40 further defining the sides of the pant). In the illustrated embodiment, the central portion 38 extends from the front waist region 22 through the crotch region 26 to the back waist region 24 of the training pant 20.

In one suitable embodiment and as seen in FIG. 2, the front side portions 40, the back side portions 42, and the central portion 38 are formed from the same sheet of material. In other suitable embodiments, one or more of the front side portions 40, the back side portions 42, and/or the central portion 38 may be formed from two or more separate elements. For example, in one suitable embodiment, the front side portions 40 and/or the back side portions 42 can be formed separately from and attached to the central portion 38.

The chassis 34 may comprise any suitable material including, for example and without limitation, a liquid permeable material that provides a generally cloth-like texture. The chassis 34 can be a single layer of material, or a multi-layered laminate structure. The chassis 34 or portions thereof may also be made of those materials of which the liquid permeable bodyside liner 48 is made. In other suitable embodiments, it is contemplated that the chassis 34 can be liquid impermeable. It is further contemplated that the chassis 34 can be vapor impermeable or vapor permeable (i.e., "breathable"). One suitable "breathable" material is composed of a microporous polymer film or a nonwoven fabric that has been coated or otherwise treated to impart a desired level of liquid impermeability.

It is also contemplated that the chassis 34 may be stretchable, and more suitably elastic. In particular, the chassis 34 is suitably stretchable and more suitably elastic in at least the transverse, or circumferential direction of the pant 20. In other embodiments, the chassis 34 may be stretchable, and more suitably elastic, in both the transverse and the longitudinal direction. It is contemplated that the chassis 34 can be stretchable in any suitable direction.

As seen in FIG. 1, the training pant 20 includes an elasticized waistband system, indicated generally at 21, configured to fully encircle the waist of the wearer during use. Referring now to FIGS. 1-3, the elasticized waistband system 21 of the illustrated embodiment includes a bodyside front waist elastic member 94, a bodyside rear waist elastic member 96, a garment-side front waist elastic member 98, and a garment-side rear waist elastic member 100. The waist elastic members 94, 96, 98, 100 can be formed of any suitable elastic material. Exemplary suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate.

In one suitable embodiment, for example, the waist elastic members 94, 96, 98, 100 comprise a plurality of dry-spun coalesced multifilament spandex elastomeric threads sold under the trade name LYCRA® and available from Invista of Wichita, Kans., U.S.A. In another suitable embodiment, the waist elastic members 94, 96, 98, 100 comprise a vertical filament laminate (VFL) material. A VFL is a composite material having at least one gatherable layer such as a non-woven material and at least one elastic layer. One type of vertical filament laminate is disclosed, for example, by U.S. Pat. No. 6,916,750 to Thomas et al., which is incorporated herein by reference. In another suitable embodiment, the waist elastic members 94, 96, 98, 100 comprise an elastic nonwoven composite having an apertured elastic film laminated to one or more nonwoven web materials, examples of which are described in U.S. Pat. No. 7,803,244 issued Sep. 28, 2010 to Siqueira et al., and U.S. Pat. No. 8,361,913 issued Jan. 29, 2013 to Siqueira et al., both of which are incorporated herein by reference. Other suitable elastic materials include single- and dual-faced spandex laminates, stretch-bonded laminates (SBL), and continuous filament stretch-bonded laminates (CFSBL), examples of which are described in U.S. Pat. No. 5,385,775 issued Jan. 31, 1995 to Wright; U.S. Pat. No. 6,057,024 issued May 2, 2000 to Mleziva et al.; and U.S. Pat. No. 6,969,441 issued Nov. 29, 2005 to Welch et al., all of which are incorporated herein by reference.

Although the elasticized waistband system 21 is illustrated and described as including bodyside front and rear waist elastic members 94, 96 and garment-side front and rear waist elastic members 98, 100, it is understood that in alternative embodiments the elasticized waistband system 21 may include any combination of the bodyside front waist elastic member 94, the bodyside rear waist elastic member 96, the garment-side front waist elastic member 98, and/or the garment-side rear waist elastic member 100. In the illustrated embodiment, each elastic member 94, 96, 98, 100 is generally rectangular in shape. Although the waist elastic members 94, 96, 98, 100 are illustrated and described as being generally rectangular, it is understood that the waist elastic members may have any suitable shape. In one embodiment, for example, the garment-side waist elastic members 98, 100 include undulated and/or scalloped edges.

As seen in FIGS. 2 and 3, the top edges of the front waist elastic members 94, 98 of the illustrated embodiment are generally aligned with the front waist edge 30 of the training pant 20, and the top edges of the rear waist elastic members 96, 100 of the illustrated embodiment are generally aligned with the back waist edge 32 of the training pant 20. It is understood, however, that the top edges of one or more of the waist elastic members 94, 96, 98, 100 can be spaced from the front waist edge 30 and/or the back waist edge 32. That is, the top edges of the front waist elastic members 94, 98 can be spaced either above or below the front waist edge 30 of the training pant 20, and/or the rear waist elastic members 96, 100 can be spaced either above or below the back waist edge 32 of the training pant 20. In one suitable embodiment, for example, the bodyside front waist elastic member 94 and the garment-side front waist elastic member 98 extend beyond the front waist edge 30, and the bodyside front waist elastic member 94 and the garment-side front waist elastic member 98 are bonded to one another such that the chassis 34 is not visible along the front waist edge 30. Additionally or alternatively, the body-side rear waist elastic member 96 and the garment-side rear waist elastic member 100 extend beyond the back waist edge 32, and the body-side rear waist elastic member 96 and the garment-side rear waist elastic member 100 are bonded to one another such that the chassis 34 is not visible along the back waist edge 32.

In the illustrated embodiment, the top edges of the bodyside waist elastic members 94, 96 are substantially aligned with the top edges of a corresponding garment-side waist elastic member 98, 100. Further, the side edges of the bodyside waist elastic members 94, 96 are substantially aligned with the side edges of a corresponding garment-side waist elastic member 98, 100. As a result, the corresponding bodyside and garment side waist elastic members 94, 96, 98, 100 have a unitary appearance similar to that of waistbands employed in reusable underwear. Further, because the bodyside waist elastic members 94, 96 are at least partially aligned with the garment-side waist elastic members 98, 100, the elasticized waistband system 21 has an increased thickness where the bodyside waist elastic members 94, 96 are aligned with the garment-side waist elastic members 98, 100. Such an increased thickness facilitates gripping and donning the training pant 20, particularly for infants or toddlers whose motor skills are not fully developed. In one suitable embodiment, for example, the thickness of the training pant 20 along the elasticized waistband system is between about 1.0 millimeters and about 6.0 millimeters and, more suitably, between about 2.0 millimeters and about 5.0 millimeters.

As illustrated in FIGS. 2 and 3, each of the side edges of the front and rear waist elastic members 94, 96, 98, 100 are generally aligned with the side edges 28 of training pant 20. Each of the front and rear waist elastic members 94, 96, 98, 100 extend from one side edge 28 of the training pant 20 to the other, laterally opposing side edge 28 of the training pant 20. The waist elastic members 94, 96, 98, 100 of the illustrated embodiment are configured to fully encircle the waist opening 66 (FIG. 1) and the wearer when the training pant 20 is donned in the wearing configuration. It is understood, however, that the side edges of one or more of the waist elastic members 94, 96, 98, 100 can be disposed either outward or inward of the side edges 28 of the training pant.

As illustrated in FIGS. 2 and 3, each waist elastic member 94, 96, 98, 100 has substantially the same length and width. It is understood, however, that the length and/or width of one or more of the waist elastic members 94, 96, 98, 100 may be different from the length and/or the width of the other waist elastic members. In one suitable embodiment, for example, each of the garment-side waist elastic members 98, 100 has a width greater than a width of the bodyside waist elastic members 94, 96.

The waist elastic members 94, 96, 98, 100 can be formed of any suitable elastic material including, for example, sheets, strands or ribbons of natural rubber, synthetic rubber, or thermoplastic elastomeric polymers. In one suitable embodiment, each waist elastic member 94, 96, 98, 100 is formed from the same material or materials as the other waist elastic members such that each waist elastic member has substantially the same properties (e.g., elasticity profile, coefficient of friction, softness, etc.) as the other waist elastic members. It is understood, however, that one or more waist elastic members 94, 96, 98, 100 may be formed of different materials to impart desired physical or visual properties to the waist elastic member. In one suitable embodiment, for example, the bodyside waist elastic members 94, 96 have a coefficient of friction greater than a coefficient of friction of the garment-side waist elastic members 98, 100 to facilitate maintaining the position of the training pant 20 on the wearer, and reduce friction between the training pant and garment(s) worn over the training pant.

The bodyside waist elastic members 94, 96 are attached to the body-facing side 23 of the training pant 20 (FIG. 3), and the garment-side waist elastic members 98, 100 are attached to the garment-facing side 26 of the training pant 20 (FIG. 2). In the illustrated embodiment, for example, the waist elastic members 94, 96, 98, 100 are point bonded to the chassis 34. In embodiments in which the absorbent assembly 36 is interposed between the chassis 34 and the bodyside waist elastic members 94, 96, such as the embodiment illustrated in FIGS. 1-3, the bodyside waist elastic members may also be point bonded to the absorbent assembly 36, such as to the bodyside liner 48 of the absorbent assembly 36. Alternatively, the bodyside waist elastic members 94, 96 may only be bonded to the training pant 20 along the chassis 34. In one suitable embodiment, for example, the bodyside waist elastic members 94, 96 are bonded to a body-facing side of the chassis 34, and are interposed between the absorbent assembly 36 and the chassis 34. In another suitable embodiment, the front and back ends of the absorbent assembly 36 are spaced inward from the bottom edges of the bodyside waist elastic members 94, 96, and the bodyside waist elastic members 94, 96 are bonded to the body-facing side of the chassis 34.

In the illustrated embodiment and as seen in FIGS. 1 and 2, leg elastic members 82 are disposed on the garment-facing side 25 of the chassis 34. It is contemplated that the leg elastic members 82 can be disposed on the body-facing side 23 of the chassis 34 in addition to or instead of the leg elastic members disposed on the garment-facing side 25. That is, in one suitable embodiment, the leg elastic members 82 can be disposed on both the body-facing and garment-facing sides 23, 25 of the chassis 34. In another suitable embodiment, the leg elastic members 82 can be disposed on either the body-facing side 23 or the garment-facing side 25 of the chassis 34.

As seen in FIG. 2, each of the leg elastic members 82 includes a plurality of elastic elements (e.g., elastic strands 83) and a carrier sheet 84 to facilitate attachment of the elastic elements to the training pant 20. It is contemplated, however, that the carrier sheet 84 can be omitted in some embodiments, and the elastic strands 83 can be attached directly to the training pant 20 (e.g., the chassis 34). Although the leg elastic members 82 are illustrated as having three elastic strands 83, the leg elastic strands may include any suitable number of elastic elements.

In the illustrated embodiment, the leg elastic members 82 are attached (e.g., bonded) to the garment-facing side 25 of the chassis 34 and positioned generally in the crotch region 26 of the absorbent training pant 20. As illustrated in FIG. 2, the leg elastic members 82 are aligned with the respective side edge 28 of the training pant 20. More specifically, each of the illustrated leg elastic members 82 is coterminous with the respective side edge 28. It is understood, however, that the leg elastic members 82 can have any suitable arrangement. The leg elastic members 82 can be formed from any suitable elastic material, such as, for example, the elastic materials described above as being suitable for the waist elastic members 94, 96, 98, 100.

Referring now to FIG. 3, the absorbent assembly 36 of the illustrated embodiment is attached to the chassis 34 along at least the crotch region 26 of the absorbent training pant 20 by an adhesive, ultrasonic bonds, thermal bonds, pressure bonds, or the like. Suitable adhesives can be applied continuously or intermittently as beads, a spray, parallel swirls, or the like. Suitable ultrasonic bonds, pressure bonds, and/or thermal bonds can be formed continuously or intermittently along the absorbent assembly 36 to effect the attachment of the absorbent assembly 36 to the chassis 34. In the illustrated embodiment, the absorbent assembly 36 is permanently attached to the chassis 34. The term "permanently attached" is synonymous with terms such as "permanently joined," "permanently adhered," and "permanently bonded," and is intended herein to refer to an attachment that is generally not releasable without some damage or substantially reduced functionality of the components that are permanently attached. In another suitable embodiment, the absorbent assembly 36 can be releasably attached to the chassis 34 by refastenable fasteners suitable for absorbent articles, such as adhesive fasteners, cohesive fasteners, mechanical fasteners (e.g., interlocking geometric shaped materials, such as hooks, loops, bulbs, mushrooms, arrowheads, balls on stems, male and female mating components, buckles, snaps) or the like.

While the absorbent assembly 36 illustrated in FIG. 3 is shown and described herein as being attached to the chassis 34 along the crotch region 26, it is contemplated that the absorbent assembly 36 may be attached to the chassis 34 along any one or more of the crotch region 26, the front waist region 22, and/or the back waist region 24, without departing from the scope of this disclosure. Further, the absorbent assembly 36 may be attached to the chassis 34 along any suitable length and/or area of the chassis 34.

As seen in FIG. 3, the illustrated absorbent assembly 36 is generally rectangular in shape, although it is contemplated that the absorbent assembly 36 may have other suitable shapes without departing from the scope of the present disclosure. In the illustrated embodiment, the front and back ends of the absorbent assembly 36 define respective portions of the front and back waist edges 30, 32 of the training pant 20. It is contemplated, however, that the front end and/or back end of the absorbent assembly 36 can be spaced inward from the front and back waist edges 30, 32 of the training pant 20. In such an embodiment, the front and back waist edges 30, 32 of the training pant 20 are defined solely by the chassis 34. As illustrated in FIG. 3, the side edges of the absorbent assembly 36 can be spaced slightly inward from the side edges 28 of the absorbent training pant 20. In other suitable embodiments, the opposite side edges of the absorbent assembly 36 can form portions of the side edges 28 of the absorbent training pant 20.

In one suitable embodiment and as illustrated in FIG. 3, the absorbent assembly 36 comprises a liquid impermeable backsheet 46 and a bodyside liner 48 attached to the backsheet in a superposed relation by suitable means such as adhesives, ultrasonic bonds, pressure bonds, thermal bonds or other conventional techniques. An absorbent structure (or absorbent core) 50 is disposed between the backsheet 46 and the bodyside liner 48. A pair of containment flaps 52 is integrally formed from the absorbent assembly 36 for inhibiting the lateral flow of body exudates.

In one suitable embodiment, the backsheet comprises a material which is substantially liquid impermeable. The backsheet 46 can be a single layer of liquid impermeable material, or may comprise a multi-layered laminate structure in which at least one of the layers is liquid impermeable. Multiple layers of the backsheet 46 may be suitably joined together by an adhesive, ultrasonic bonds, pressure bonds, thermal bonds, or the like. Suitable adhesives can be applied continuously or intermittently as beads, a spray, parallel swirls, or the like.

The backsheet 46 can be both liquid and vapor impermeable, or, more suitably, it may be liquid impermeable and vapor permeable. The backsheet 46 can be manufactured from a thin plastic film, although other flexible liquid impermeable materials may also be used. The backsheet 46 prevents waste material from wetting articles, such as bed sheets and clothing, as well as the wearer and caregiver. In one suitable embodiment, the liquid impermeable material can permit vapors to escape from the interior of the disposable absorbent article, while still preventing liquids from passing through the backsheet 46. One suitable "breathable" material is composed of a microporous polymer film or a nonwoven fabric that has been coated or otherwise treated to impart a desired level of liquid impermeability.

It is also contemplated that the backsheet 46 may comprise a liquid permeable material, or the backsheet 46 may be omitted from the absorbent assembly 36 altogether. In such embodiments, the chassis 34 suitably comprises a liquid impermeable material to provide a liquid barrier to body exudates. In one embodiment in which the backsheet 46 is omitted, the bodyside liner 48 is attached to the chassis 34 such that the absorbent structure 50 is disposed between the bodyside liner 48 and the inner surface of the chassis 34. In another suitable embodiment, both the absorbent structure 50 and the bodyside liner 48 are attached to the chassis 34.

It is also contemplated that the backsheet 46 may be stretchable, and more suitably elastic. In particular, the backsheet 46 is suitably stretchable and more suitably elastic in at least the transverse, or circumferential direction of the pant 20. In other embodiments the backsheet 46 may be stretchable, and more suitably elastic, in both the transverse and the longitudinal direction.

The bodyside liner 48 is suitably compliant, soft-feeling, and non-irritating to the wearer's skin. The bodyside liner 48 is also sufficiently liquid permeable to permit liquid body exudates to readily penetrate through its thickness to the absorbent structure 50. Further, the bodyside liner 48 can be less hydrophilic than the absorbent structure 50 to present a relatively dry surface to the wearer and permit liquid to readily penetrate through its thickness. The hydrophilic/hydrophobic properties can be varied across the length, width and/or depth of the bodyside liner 48 and absorbent structure 50 to achieve the desired rate of fluid intake and dryness.

A suitable bodyside liner 48 may be manufactured from a wide selection of web materials, such as porous foams, reticulated foams, apertured plastic films, woven and nonwoven webs, or a combination of any such materials. For example, the bodyside liner 48 may comprise a meltblown web, a spunbonded web, or a bonded-carded-web composed of natural fibers, synthetic fibers or combinations thereof. The bodyside liner 48 may be composed of a substantially hydrophobic material, and the hydrophobic material may optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 48 or can be selectively applied to particular sections of the bodyside liner, such as the medial section along the longitudinal center line.

The bodyside liner 48 may also be stretchable, and more suitably it may be elastomeric. Suitable elastomeric materials for construction of the bodyside liner 48 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers. The bodyside liner 48 can also be made from extensible materials as are described in U.S. patent application Ser. No. 09/563,417 filed on May 3, 2000 by Roessler et al. or from biaxially stretchable materials as are described in U.S. patent application Ser. No. 09/698,512 filed on Oct. 27, 2000 by Vukos et al., both references which are hereby incorporated by reference.

As seen in FIG. 3, the illustrated absorbent structure 50 is generally rectangular. It is contemplated, however, that the absorbent structure 50 can have any suitable shape and size. For example, the absorbent structure 50 can include arcuate leg cutouts (e.g., by die cutting the absorbent structure) in the crotch region 26 of the training pant 20. While the illustrated absorbent structure 50 is shown and described herein as extending from the crotch region 26 into both the front and back waist regions 22 and 24, it is contemplated that the absorbent structure may extend from the crotch region 26 into only the front waist region 22, or only the back waist region 24, without departing from the scope of this disclosure.

The absorbent structure 50 is suitably compressible, conformable, non-irritating to a wearer's skin, and capable of absorbing and retaining liquids and certain body wastes. For example, the absorbent structure 50 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent structure comprises a matrix of cellulosic fluff and superabsorbent hydrogel-forming particles. The cellulosic fluff may include a blend of wood pulp fluff. Suitable types of fluff include, for example, fluff pulp commercially available from Weyerhaeuser Company under the designation FR416 (7.5 percent Moisture) and CF416 (7.5 percent Moisture). Weyerhaeuser Company has offices in Federal Way, Wash., U.S.A.

The materials may be formed into a web structure by employing various conventional methods and techniques. For example, the absorbent structure 50 may be formed by a dry-forming technique, an air forming technique, a wet-forming technique, a foam-forming technique, or the like, as well as combinations thereof. Methods and apparatus for carrying out such techniques are well known in the art. Furthermore, the absorbent structure 50 may itself encompass multiple layers in a Z-direction (e.g., thickness) of the absorbent structure 50. Such multiple layers may take advantage of differences in absorbent capacity, such as by placing a lower absorbent capacity material layer closer to the liner 48 and a higher absorbent capacity material closer to the backsheet 46. Likewise, discrete portions of a single-layered absorbent structure may encompass higher capacity absorbents, and other discrete portions of the structure may encompass lower capacity absorbents.

Superabsorbent material is suitably present in the absorbent structure 50 in an amount of from about 0 to about 100 weight percent based on total weight of the absorbent structure 50. The absorbent structure 50 may suitably have a density within the range of about 0.10 to about 0.60 grams per cubic centimeter. Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid. Suitable superabsorbent materials are readily available from various suppliers. For example, Hysorb T 9700 superabsorbent, which is commercially available from BASF of Ludwigshafen, Germany, or Favor SXM 5600 superabsorbent, which is commercially available from Evonik of Essen, Germany.

The absorbent structure 50 may alternatively comprise a coform material. The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

In one suitable embodiment, the absorbent structure 50 is stretchable so as not to inhibit the stretchability of other components to which the absorbent structure may be adhered, such as the backsheet 46 and bodyside liner 48. After being formed or cut to a desired shape, the absorbent structure 50 may be wrapped or encompassed by a suitable wrap (not shown) that aids in maintaining the integrity and shape of the absorbent structure.

The absorbent assembly 36 is configured to contain and/or absorb exudates discharged from the wearer. For example, the containment flaps 52 are configured to provide a barrier to the transverse flow of body exudates. A flap elastic member 72 (FIG. 3) may be operatively joined with each containment flap 52. The elasticized containment flaps 52 define a partially unattached, or free, edge which assumes an upright configuration in at least the crotch region 26 of the absorbent training pant 20 to form a seal against the wearer's body during use. In one suitable embodiment, the containment flaps 52 can be located along the side edges 28 of the training pant 20, and can extend longitudinally along the entire length of the absorbent assembly 36 or may only extend partially along the length of the absorbent assembly 36.

In the illustrated embodiment, the absorbent assembly 36 also includes a surge management layer 76, which can be seen in FIG. 3, located adjacent the absorbent structure 50 (e.g., between the absorbent structure 50 and the liner 48). The surge management layer 76 helps to decelerate and diffuse surges or gushes of liquid that may be rapidly introduced into the absorbent structure 50 of the training pant 20 by the wearer. Desirably, the surge management layer 76 can rapidly accept and temporarily hold the liquid prior to releasing the liquid into the storage or retention portions of the absorbent structure 50. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, I I et al., the entire disclosures of which are hereby incorporated by reference herein.

Referring again to FIG. 1, the training pant 20 includes a pair of non-refastenable fin seams 70. One of the fin seams 70 is disposed on one side of the training pant 20 and the other fin seam is disposed on the opposite side of the pant. It is understood, however, that the fin seams 70 can be located at any suitable location on the training pant 20 and that the seams can be formed using any suitable bonding method such as, e.g., adhesive bonding, thermal bonding, pressure bonding, and combinations thereof. In one suitable bonding method, which is described in more detail below, the fin seams 70 can be formed using ultrasonic bonding.

As seen in FIG. 1, the front and back waist regions 22, 24 are attached to each other by the fin seams 70 to define a wear configuration of the pant having the waist opening 66 and a pair of leg openings 68. The waist edges 30, 32 of the absorbent training pant 20 are configured to encircle the waist of the wearer and together define the waist opening 66, and portions of the side edges 28 in the crotch region 26 generally define the leg openings 68. Each of the fin seams 70 extends at least part of the way from the waist opening 66 to the respective leg opening 68. In the illustrated embodiment, for example, each of the fin seams 70 extends approximately the entire distance between the waist opening 66 and the respective leg opening 68. It is contemplated, however, that in some suitable embodiments, the fin seams 70 can extend a distance less than the entire distance between the waist opening 66 and the respective leg opening 68.

Figure 4:
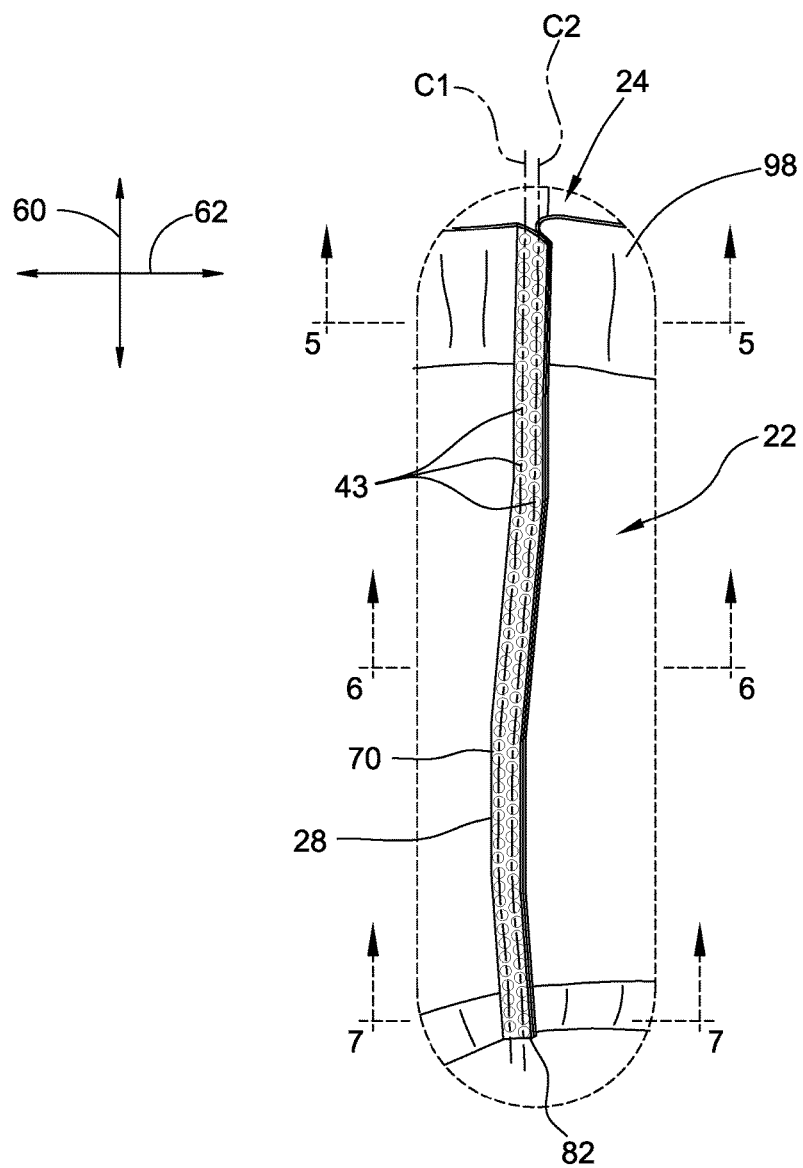
FIG. 4 is an enlarged side perspective view of one of the fin seams of the training pant of FIG. 1.

FIG. 4 is an enlarged fragmentary view taken from one of the fin seams 70 of FIG. 1. In the illustrated embodiment, the fin seams 70 are formed by point bonding the front waist region 22 of the training pant 20 to the back waist region 24 along the side edges 28 such that the body-facing surface 23 of the chassis 34 in the front waist region is bonded in face-to-face relationship with the body-facing surface of the chassis in the back waist region. As seen in FIG. 4, the illustrated fin seam 70 extends outward from the training pant 20. Thus when the training pant 20 is donned, the fin seams 70 extend away from the wearer. It is contemplated, however, that the fin seams 70 can extend inward. In such an embodiment, the fin seams 70 would extend toward the wearer when the training pant 20 is donned.

Figure 5:
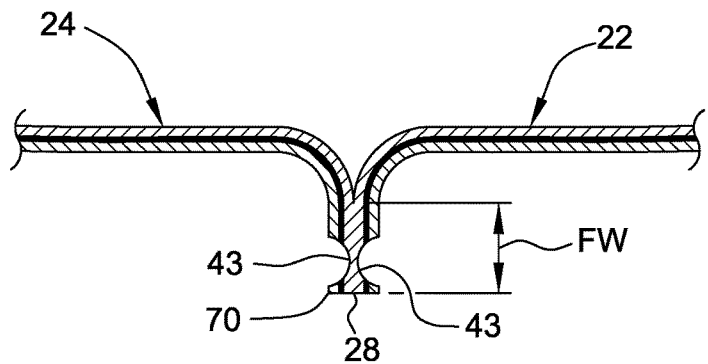
FIG. 5 is a cross-section taken along line 5-5 of FIG. 4.

In one suitable embodiment, each of the fin seams 70 has a width FW less than 5.0 mm, and more suitably less than 3 mm. Suitably, for example, each of the fin seams 70 has a width FW of about 1 mm. As seen in FIG. 5, the width FW of the fin seams 70 is a measurement of how far the fin seam extends outward from the training pant 20 in a direction generally parallel to the transverse axis 62 of the pant.

With reference still to FIG. 4, the point bonding results in a plurality of discrete point bonds 43. In one suitable embodiment, the point bonds 43 are aligned in columns (FIG. 4). In the illustrated embodiment, for example, the point bonds are aligned in two distinct columns: a first column C1 and a second column C2. It is understood, however, that the discrete point bonds 43 can be arranged in any suitable number of columns. That is, the point bonds 43 can be arranged in fewer columns (i.e., one) or more than the two columns illustrated in FIG. 4 without departing from some aspects of this disclosure. It is also understood that the point bonds can have any suitable arrangement without departing from some aspects of this disclosure.

As seen in FIG. 4, the point bonds 43 of one column are longitudinally offset relative to the point bonds in the adjacent column. As a result, the point bonds 43 are not aligned in transversely extending rows. More specifically, in the illustrated embodiment, the point bonds 43 of the first column C1 define a first longitudinal center line and the point bonds of the second column C2 define a second longitudinal center line. In one suitable embodiment, an outer periphery or boundary of the point bonds 43 defining the first column C1 are generally aligned with or extend beyond the centerline of the second column C2. Likewise, an outer periphery or boundary of the point bonds 43 defining the second column C2 are generally aligned with or extend beyond the centerline of the first column C1. Also in the illustrated embodiment, the outer periphery or boundary of the point bonds 43 contact the outer periphery or boundary of the adjacent point bonds 43.

Figure 6:
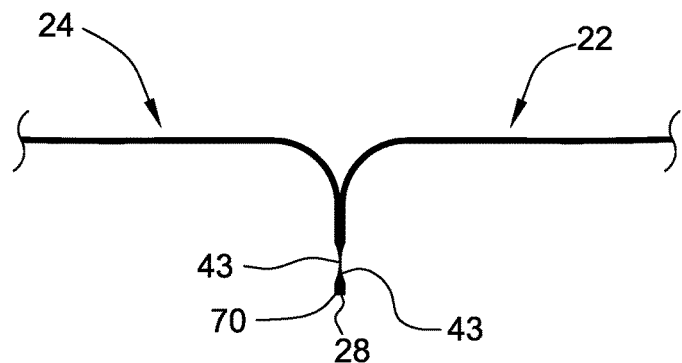
FIG. 6 is a cross-section taken along line 6-6 of FIG. 4.
Figure 7:
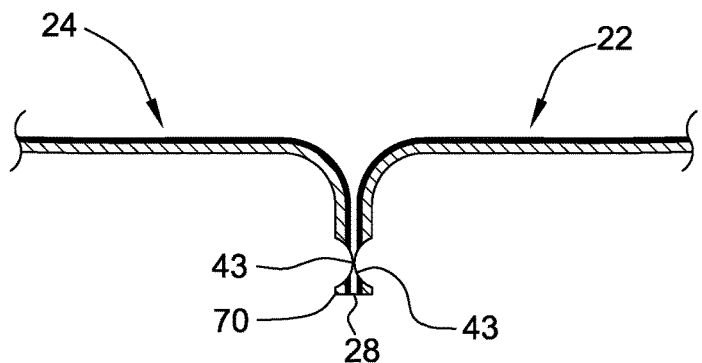
FIG. 7 is a cross-section taken along line 7-7 of FIG. 4.

In the illustrated embodiment and as best seen in FIGS. 5-7, the point bonds 43 form generally domed-shaped recesses but it is understood that the point bonds 43 can form any suitable shape or relative arrangement. In one suitable embodiment, each of the point bonds 43 is generally the same size and shape. It is understood, however, that the size and shape of point bonds 43 can differ. That is, the point bonds 43 forming the fin seam 70 can vary in size and/or shape. Suitably, however, all of the point bonds 43 forming the fin seam 70 are of the same size and shape as illustrated in FIG. 4.

In one suitable embodiment, each of the point bonds 43 has a diameter (or more broadly a greatest extent) between about 0.5 mm and about 2 mm. Suitably, for example, the diameter of each of the point bonds 43 is about 1.5 mm. As explained above, the point bonds 43 of the two columns C1, C2 overlap. In one suitable embodiment, the point bonds 43 of the adjacent columns C1, C2 overlap by about half the diameter of the point bonds. For example, in an embodiment having point bonds 43 with a diameter of 1.5 mm, the point bonds of one of the columns C1, C2 will overlap the point bonds of the other column by about 0.75 mm.

FIGS. 5-7 are cross-sections taken through various locations of the fin seam 70 of FIG. 4. Specifically, FIG. 5 is a cross-section taken through the fin seam 70 formed in the elasticized waistband system 21. As illustrated therein, the point bonds 43 are formed through the bodyside front waist elastic member 94, the bodyside rear waist elastic member 96, the garment-side front waist elastic member 98, the garment-side rear waist elastic member 100 and the underlying chassis 34. FIG. 7 is a cross-section taken through the fin seam 70 formed through the respective leg elastic member 82. As seen in FIG. 7, the point bonds 43 are formed through the leg elastic member 82 and the underlying chassis. FIG. 6 is a cross-section taken through the fin seam 70 at a location between the waistband system 21 and the leg elastic member 82. As illustrated in FIG. 6, the point bonds 43 are formed through the chassis 34.

In one suitable embodiment, the point bonds 43 formed through the waistband system 21, the leg elastic member 82 and the portion of the chassis 34 located between the waistband system and the leg elastic member are substantially the same. That is, the point bonds 43 throughout the length of the fin seam 70 have substantially the same size and shape and are applied in the same pattern and at the same density. In another suitable embodiment, the point bonds 43 formed along the length of the fin seam 70 can differ in size or shape or be applied in different patterns or at different densities. For example, the point bonds 43 formed through the waistband system 21 can differ from the point bonds formed through the leg elastic member 82 and/or the portion of the chassis 34 located between the waistband system and the leg elastic member. In another example, the point bonds 43 formed through the leg elastic members 82 can differ from the point bonds formed through the waistband system 21 and/or the portion of the chassis 34 located between the waistband system and the leg elastic member.

A plurality of the training pants 20 illustrated in FIGS. 1-7 can be manufactured using any suitable manufacturing method. In one suitable method of manufacturing, each training pant 20 of the plurality of the training pant is folded at a suitable folding station. More specifically, each of the training pants 20 are folded about a fold line generally bisecting the training pant (i.e., folded about the transverse axis 62. As such, the front and back waist regions 22, 24 of each training pant 20 are positioned in facing relationship. More specifically, the bodyfacing surface 23 of front region 22 of the chassis is positioned in face-to-face relationship with the bodyfacing surface of the back region 24 as illustrated in FIG. 8.

Figure 8:
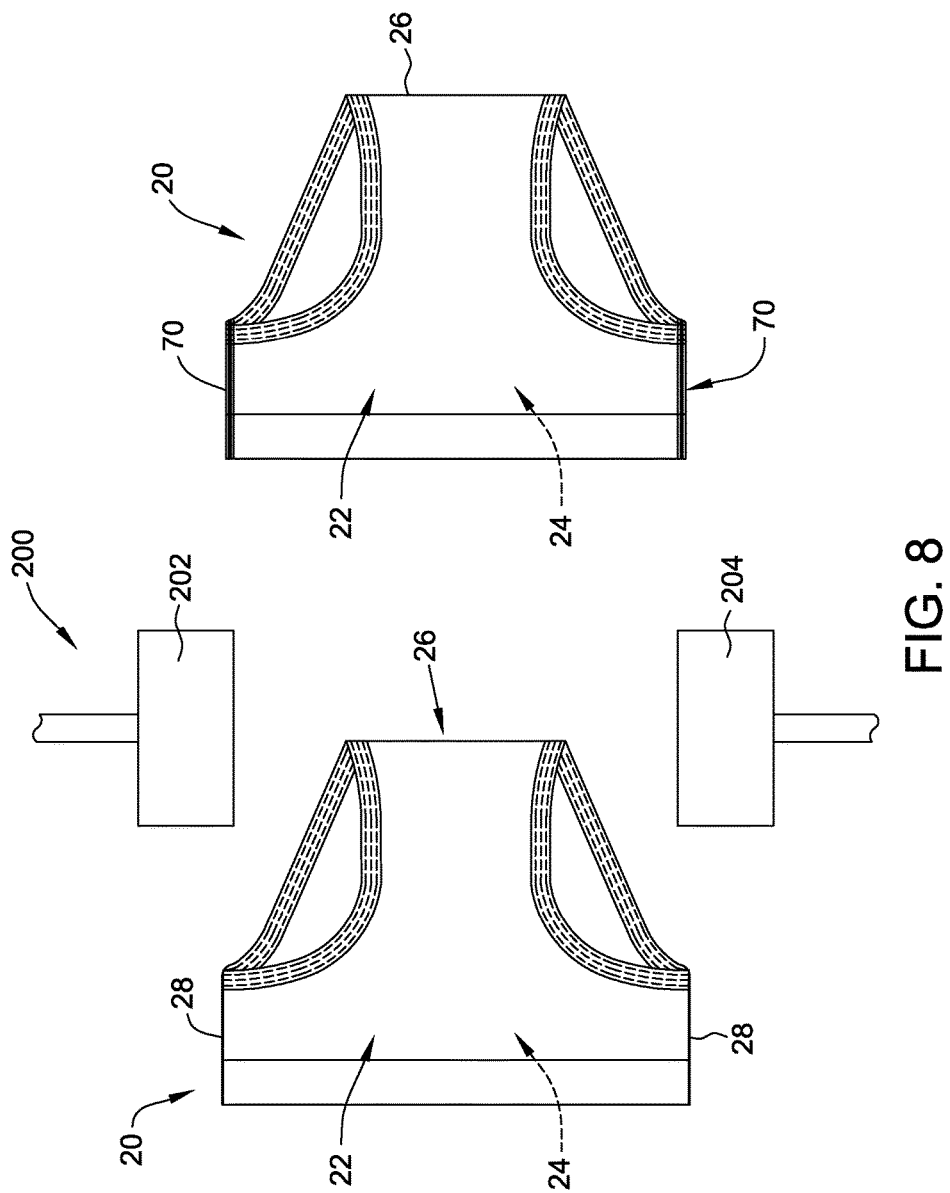
FIG. 8 is a schematic illustrating one suitable method for bonding the fin seams of the absorbent article illustrated in FIGS. 1-7.

Once the training pant 20 is folded, the fin seams 70 can be formed at a bonding and slitting station, indicated generally at 200 in FIG. 8. As seen in FIG. 8, the illustrated bonding station 200 comprises a first bonding and slitting device 202 and a second bonding and slitting device 204. The first bonding and slitting device 202 is configured to form the fin seam 70 on one of the sides (i.e., along one of the side edges 28) of the training pant 20, and the second bonding and slitting device 204 is configured to form the fin seam on the opposite side (i.e., along the other side edge).

In the illustrated embodiment, the first bonding and slitting device 202 is independent of the second bonding and slitting device 204. That is, the first bonding and slitting device 202 can be operated independently of the second bonding and slitting device 204. In another suitable embodiment, the first and second bonding and slitting devices 202, 204 can be dependent on each other. In one such embodiment, for example, the first bonding and slitting device 202 and the second bonding and slitting device 204 can be formed on a single roll in spaced relationship with each other.

In one suitable embodiment and as illustrated in FIG. 8, both the first and second bonding and slitting devices 202, 204 are substantially the same and comprise suitable bonding devices. It is understood that any suitable bonding device can be used without departing from some aspects of this disclosure. Each of the first and second bonding and slitting devices 202, 204 comprise a first bonding member and a seconding member capable of bonding the fin seam 70. More specifically in the illustrated embodiment, the first and second bonding and slitting devices 202, 204 each comprise a rotary ultrasonic horn 208 (broadly, the first bonding member) and a cooperating rotary anvil 210 (broadly, the second bonding member) adapted to ultrasonically bond and, more specifically, point bond the front region 22 of the chassis 34 to the back region 24 to define the fin seams 70 and to trim, score, perforate or otherwise weaken the material outboard of the point bonds from both the front and back regions of the chassis. The horn 208 and anvil 210 cooperatively define, at least in part, the ultrasonic bonding device. Suitable rotary ultrasonic horns are available from Aurizon Ultrasonics, LLC of Kimberly, Wis., U.S.A.

Since the first and second bonding and slitting devices 202, 204 are the same, the operation of only the first bonding and slitting device 202 is descripted herein with the understanding that the second bonding and slitting device 204 operates in the same manner. With reference now to FIGS.

9 and 11, which illustrates the operation of the first bonding and slitting device 202, the ultrasonic horn 208 and anvil 210 are configured to counter-rotate with respect to each other. That is, the ultrasonic horn 208 rotates in one direction and the anvil rotates in the opposite direction. In the illustrated embodiment, for example, the ultrasonic horn 208 rotates in a clockwise direction and the anvil 210 rotates in a counterclockwise direction.

A suitable horn drive (not shown) can be operatively connected to the ultrasonic horn 208 to rotate the ultrasonic horn, and a suitable anvil drive (not shown) can be operatively connected to the anvil 210 to rotate the anvil. The horn drive and anvil drive may be separate driving mechanisms, or may be the same driving mechanism. In one suitable embodiment, the horn 208 may be rotated by a driving mechanism, and the anvil member may be driven by the contact pressure between the horn, the training pant 20 and the anvil 210. Suitable driving mechanism can include, for example, take-offs from a powered line shaft, motors, engines, electric motors or the like, as well as combinations thereof.

Figure 9:
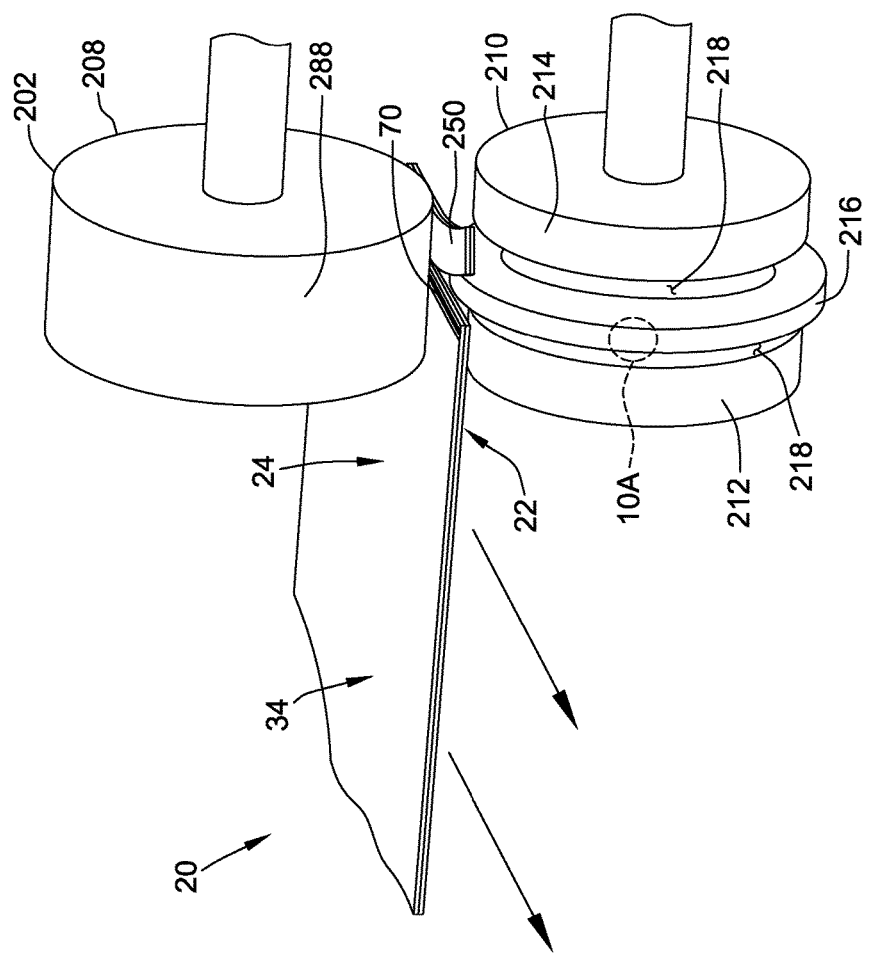
FIG. 9 is a perspective view of one embodiment of a bonding and slitting device suitable for use in the method illustrated in FIG. 8.
Figure 11:
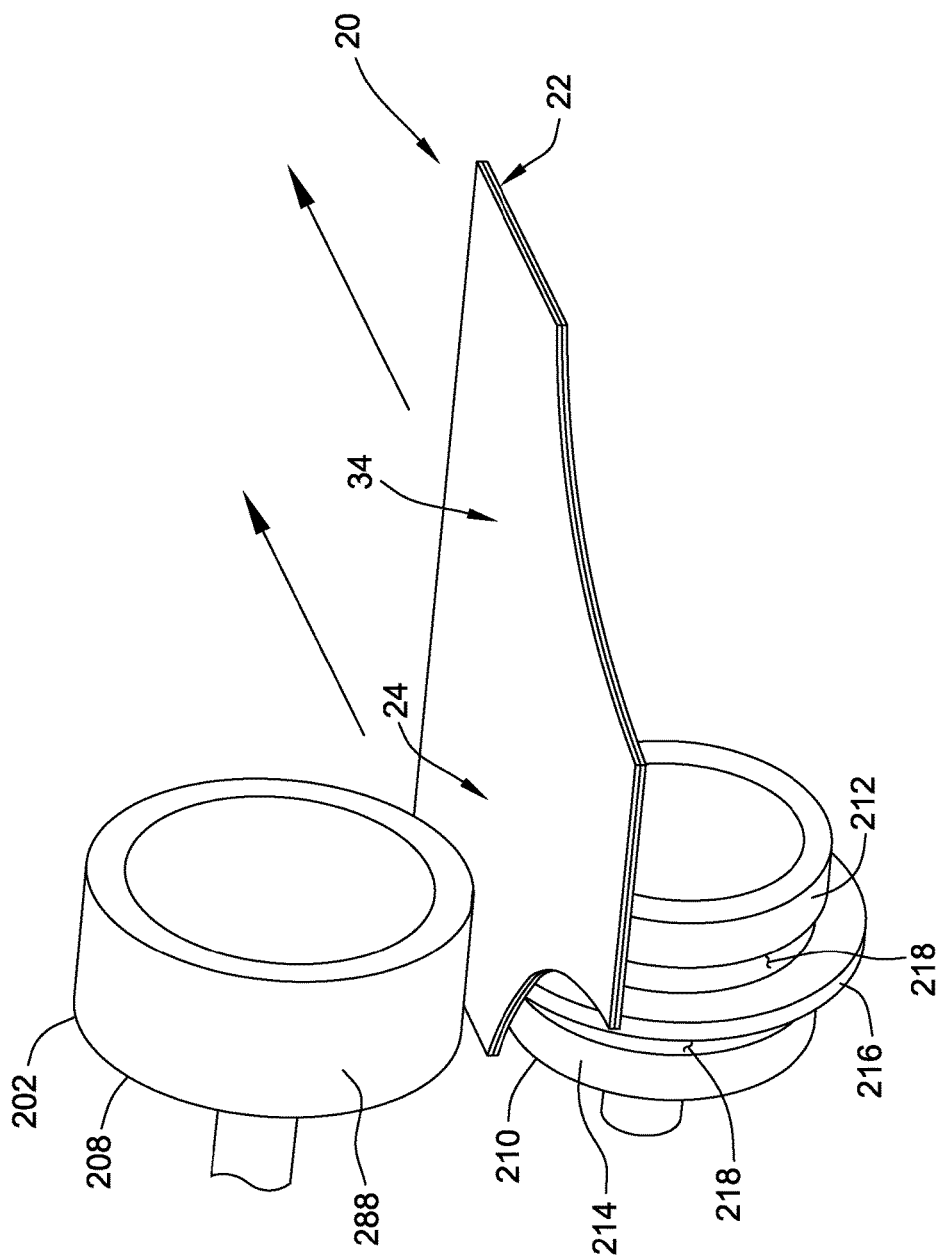
FIG. 11 is another perspective view of the bonding and slitting device of FIG. 9.

As seen in FIGS. 9 and 11, the illustrated ultrasonic horn 208 is a circular cylinder having an outer peripheral surface 288. It is understood, however, that the ultrasonic horn 208 can have any suitable shape and/or configuration. In one suitable embodiment, the ultrasonic horn 208 can be rotated by its corresponding drive to provide an outer peripheral speed at its outer peripheral surface 288. Suitably, the outer peripheral speed of the ultrasonic horn 208 can be between about 100 m/min and about 600 m/min, and more suitably between about 200 m/min and about 400 m/min. For example, in one suitable embodiment, the outer peripheral speed of the ultrasonic horn 208 is about 300 m/min. It is understood, however, the ultrasonic horn 208 can operate at any suitable outer peripheral speed without departed from some aspects of this invention. It is further understood that the outer peripheral speed may be substantially constant, or may be non-constant (i.e., variable) as desired.

In one suitable embodiment, the rotatable anvil 210 can be rotated by its corresponding drive to provide a desired anvil speed at its outer peripheral surface. Suitably, the outer peripheral speed of the anvil 210 can be between about 100 m/min and about 600 m/min, and more suitably between about 200 m/min and about 400 m/min. For example, in one suitable embodiment, the outer peripheral speed of the anvil 210 is about 300 m/min. It is understood, however, the anvil 210 can operate at any suitable outer peripheral speed without departed from some aspects of this invention. It is further understood that the outer peripheral speed may be substantially constant, or may be non-constant (i.e., variable) as desired.

With reference still to FIGS. 9 and 11, the illustrated anvil 210 comprises an outer disk 212, an inner disk 214, and a contact element 216 disposed between the outer and inner disks. In the illustrated embodiment, the contact element 216 is spaced from the inner and outer disks by a pair of annular recesses 218. It is contemplated that the anvil 210 can have any suitable configuration without departing from some aspects of this disclosure.

Figure 10A:
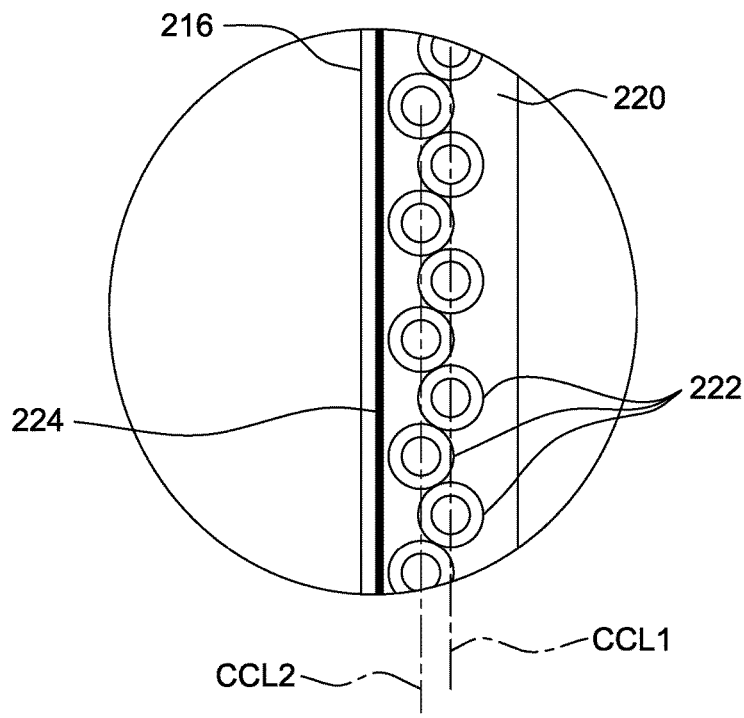
FIG. 10A is an enlarged perspective view taken from FIG. 9 and illustrating one suitable bonding pattern.

The contact element 216 is configured to cooperate with the horn 208 to ultrasonically point bond the front region 22 of the chassis 34 to the back region 24 to define the fin seams 70 and to trim or otherwise act on material outboard of the point bonds from both the front and back regions of the chassis. More specifically and as illustrated in FIG. 10A, which is an enlargement of a portion of the contact element 216 of FIG. 9, the contact element has an engagement surface 220 extending about the circumference of the contact element 216 having a plurality of bonding elements 222 adapted to point bond the front region 22 and the back region 24 of the chassis 34, and a slitter 224 adapted to cut both the front region 22 and the back region 24. It is contemplated, however, that the slitter 224 can be adapted to weaken (score, perforate) rather than cut one of or both the front region 22 and the back region 24 of the chassis 34 to facilitate later removal of material outboard of the point bonds 43.

The bonding elements 222 of the contact element 216 can have any suitable configuration (including, e.g., size, shape, spacing) to achieve the desired bond pattern. In the illustrated embodiment, the bonding elements 222 encircle the full circumference of the contact element 216. In other words, the bonding elements 222 are provided continuously over the entire circumferential distance of the contact element 216. It is contemplated, however, that the bonding elements 222 can extend over only a portion or discrete portions of the circumference of the contact element 216. It is also contemplated that bonding elements 222 can be provided on ultrasonic horn 288 in addition to or instead of the bonding elements on the contact element 216 of the anvil 210.

In the illustrated embodiment, the bonding elements 222 are configured to achieve the plurality of discrete point bonds 43 illustrated in FIG. 4. More specifically, the bonding elements 222 of FIG. 10A are aligned in two distinct columns. It is understood, however, that the bonding elements 222 can be aligned in any suitable number of columns. That is, the bonding elements 222 can be aligned in fewer columns (i.e., one) or more than the two columns illustrated in FIG. 10A without departing from some aspects of this disclosure.

As seen in FIG. 10A, the bonding elements 222 of one column are longitudinally offset relative to the bonding elements 222 in the adjacent column. As a result, the bonding elements 222 are not aligned in transversely extending rows. More specifically, in the illustrated embodiment, a circumferentially extending centerline CCL1 through one column of bonding elements 222 is spaced from a circumferentially extending centerline CCL2 through the other column of bonding elements 222 by a distance D1. While the distance D1 can be any suitable distance, in one suitable embodiment the distance D1 is between about 0.5 mm and about 2 mm, and more suitable between about 0.6 mm and about 1 mm. For example, in the illustrated embodiment, the distance D1 is approximately 1 mm.

Figure 10B:
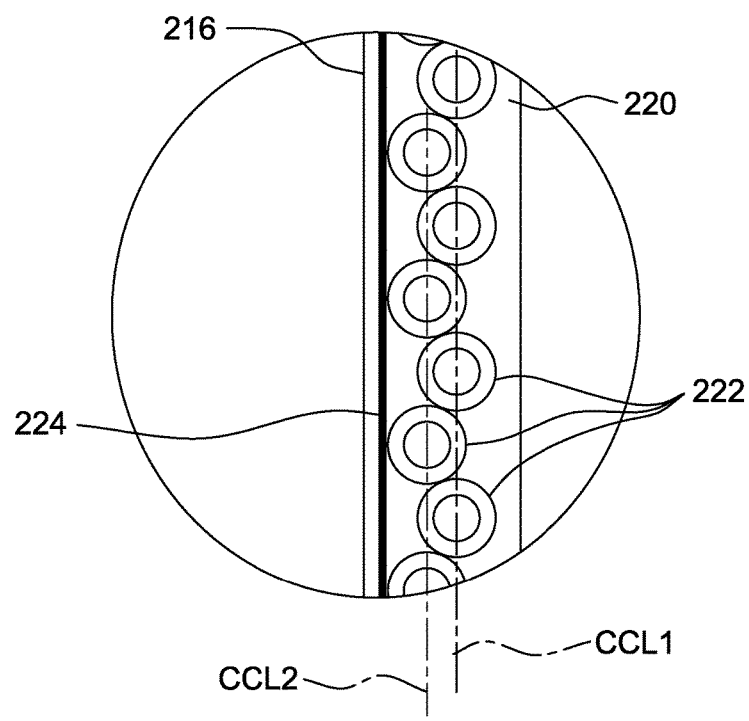
FIG. 10B is an enlarged perspective view similar to FIG. 10A but illustrating another suitable bonding pattern.

In the illustrated embodiment, the bonding elements 222 are generally frustum nubs but it is understood that the bonding elements can have any suitable shape or relative arrangement. In one suitable embodiment, each of the bonding elements 222 has a maximum diameter (or more broadly a greatest extent) between about 0.5 mm and about 2 mm. Suitably, for example, the diameter of each of the bonding elements 222 illustrated in FIG. 10A is about 1 mm. In another suitable embodiment, which is illustrated in FIG. 10B, the diameter of each of the bonding elements 222 is about 1.5 mm. It is understood that the bonding elements 222 can have any suitable diameter (or greatest extent).

In one suitable embodiment, the bonding elements 222 disposed on the contact element 216 are all the same size and shape and are arranged in the same pattern and at the same density about the entire circumference of the contact element. It is understood, however, that the bonding elements 222 can extend about only a portion of the circumference of the contact element 216. It is further understood that the bonding elements 222 disposed on the contact element 216 can vary in size, shape, pattern, and/or density about the circumference of the contact element 216. In one such embodiment, the contact element 216 has a plurality of zones of bonding elements 222 with each zone having at least one of a different size, shape, pattern, and/or density. Each of the zones of bonding elements 222 can be phased (or registered) with a portion or portions of the fin seam 70. For example, one zone of bonding elements 222 can be phased with the portion of the fin seam 70 comprising the waistband system 21, another zone of bonding elements can be phased with the portion of the fin seam comprising the leg elastic members 82, and yet another zone of bonding elements can be phased with the portion of the chassis 34 located between the waistband system 21 and the leg elastic member 82.

As seen in FIGS. 9 and 11, the slitter 224 of the illustrated embodiment of the anvil 210, which is continuous about the circumference of the contact element 216, is aligned with the outer edges of the outer most column of bonding elements 222. More specifically, in the illustrated embodiment, the slitter 224 contacts the outer edges of the outer most column of bonding elements 222. It is contemplated that in other suitable embodiments, the slitter 224 can be slightly spaced from the bonding elements 222 such that the slitter is free from contact with the bonding elements. For example, in one suitable embodiment, the slitter 224 can be spaced from the bonding elements 222 by a distance between about 0.5 mm and about 5 mm.

The slitter 224 of the contact element 216 of the anvil 210 is adapted to trim material 250 from both the front region 22 and the back region 24 of the chassis 34 simultaneously as the bonding elements 222 are bonding the front and back regions (FIG. 9). Thus, the front region 22 and the back region 24 of the chassis 34 are being cut and bonded at the same time as the chassis passes through the first bonding and slitting device 202.

An ultrasonic exciter (not shown) is operatively connected to the ultrasonic horn 208 to direct a sufficient amount of ultrasonic power into the horn through suitable, ultrasonic wave-guides, booster members, and connection/transmission components. In one suitable embodiment, for example, the ultrasonic exciter is operatively connected to the horn 208, and is capable of providing an operative amount of ultrasonic energy at a frequency within the range of about 15-60 KHz (Kilo-Hertz). Suitable ultrasonic exciters, ultrasonic connectors, ultrasonic boosters and ultrasonic wave-guides are well known in the art and are available from commercial vendors. Examples of suitable ultrasonic power systems include, but are not limited to, a Model 20A3000 system available from Dukane Ultrasonics, which has offices located in St. Charles, Ill.; and a Model 2000CS system available from Herrmann Ultrasonics, which has offices located in Schaumburg, Ill.

In operation, a plurality of folded training pants 20 are fed in succession to the bonding and slitting station, indicated generally at 200 in FIG. 8. In the illustrated embodiment, the training pants 20 are fed in the machine direction with crotch region 26 first but it is understood that the training pants can be fed to the bonding and slitting station 200 in any suitable manner including, for example, with the crotch region 26 last or in a cross-machine direction.

At the bonding station 200, the first bonding and slitting device 202 forms the fin seam 70 on one side (i.e., along one of the side edges 28) of the training pant 20, and the second bonding and slitting device 204 forms the fin seam on the opposite side (i.e., along the other side edge). More specifically, the training pants 20, which as mentioned above are being fed crotch region 26 first in the illustrated embodiment, pass through the nip defined by the ultrasonic horn 208 and the anvil 210 for each of the first and second bonding and slitting devices 202, 204. The horn 208 of each of the devices 202, 204, which is ultrasonically operating, cooperates with the respective anvil 210 to point bond and trim the front and back waist regions 22, 24 of the chassis 34 adjacent the side edges 28.

As explained above, the contact element 216 of each anvil 210 is configured to cooperate with the respective horn 208 to ultrasonically point bond via the bonding elements 222 the front region 22 of the chassis 34 to the back region 24 to define the fin seams 70 and to trim material outboard of the point bonds from both the front and back regions of the chassis. The slitter 224 of the contact element 216 of each of the anvils 210 trims material 250 from both the front region 22 and the back region 24 of the chassis 34 simultaneously as the bonding elements 222 bond the front and back regions to form the fin seams 70. Thus, the front region 22 and the back region 24 of the chassis 34 are cut and bonded at the same time as the chassis passes through the first and second bonding and slitting devices 202, 204.

As the training pant 20 passes through the bonding station 200, the portion of the fin seam 70 extending through the respective leg elastic member 82 is formed first. As seen in FIG. 7, the point bonds 43 formed by the bonding elements 222 are formed through the leg elastic member 82 and the underlying chassis. Moreover, the slitter 224 trims material from both the leg elastic member 82 and the underlying chassis 34 (i.e., the front region 22 and the back region 24). As illustrated in FIG. 7, the material defining the side edge 28, which was trimmed by the slitter, has a first thickness.

FIG. 6 is a cross-section taken through the fin seam 70 at a location between the waistband system 21 and the leg elastic member 82. As illustrated in FIG. 6, the point bonds 43 are formed by the bonding elements 222 through the chassis 34. The slitter 224 trims material from the underlying chassis 34 (i.e., the front region 22 and the back region 24). As illustrated in FIG. 6, the material defining the side edge 28, which was trimmed by the slitter, has a second thickness which is substantially less than the first thickness.

FIG. 5 is a cross-section taken through the fin seam 70 at the waistband system 21. The point bonds 43 are formed via the bonding elements 222 through the bodyside front waist elastic member 94, the bodyside rear waist elastic member 96, the garment-side front waist elastic member 98, the garment-side rear waist elastic member 100 and the underlying chassis 34. The slitter 224 trims material from the waistband system 21 and the underlying chassis 34 (i.e., the front region 22 and the back region 24). As illustrated in FIG. 5, the material defining the side edge 28, which was trimmed by the slitter, has a third thickness which is significantly greater than both the first and second thicknesses. Thus, as the training pants 20 are fed through the bonding station 200, the ultrasonic horn 208 and anvil 210 have to accommodate for the three different thicknesses of the fin seams 70.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A bonding and slitting device adapted to form fin seams in absorbent articles having a front waist region, a back waist region, and a crotch region extending between the front waist region and the back waist region, the device comprising:
    a first bonding member; and
    a second bonding member having a contact element configured to cooperate with the first bonding member to bond the front region to the back region to define the fin seams, the contact element having an engagement surface and a slitter extending from the engagement surface, the slitter being configured to simultaneously act on material outboard of the bonds from both the front and back regions.

2. The bonding and slitting device as set forth in claim 1 wherein the contact element includes a plurality of bonding elements adapted to point bond the front region and the back region.

3. The bonding and slitting device as set forth in claim 2 wherein the contact element has a circumference and the bonding elements extend continuously about the circumference of the contact element.

4. The bonding and slitting device as set forth in claim 2 wherein the bonding elements are aligned in at least two circumferentially extending columns, each column being offset relative to an adjacent column.

5. The bonding and slitting device as set forth in claim 4 wherein each of the columns of bonding elements define a circumferentially extending centerline, each centerline being spaced from an adjacent centerline by a distance between 0.5 mm and 2 mm.

6. The bonding and slitting device as set forth in claim 2 wherein at least some of the bonding elements are frustum nubs.

7. The bonding and slitting device as set forth in claim 2 wherein the slitter is spaced from the bonding elements by a distance between 0.5 mm and 5 mm.

8. The bonding and slitting device as set forth in claim 1 wherein the contact element has a circumference and the slitter extends continuously about a circumference of the contact element.

9. The bonding and slitting device as set forth in claim 1 wherein the first bonding member is a rotary ultrasonic horn and the second bonding member is a rotary anvil, the ultrasonic horn and the anvil being configured to counter-rotate with respect to each other.

10. A bonding and slitting device adapted to form fin seams in absorbent articles having a front waist region, a back waist region, and a crotch region extending between the front waist region and the back waist region, the device comprising:
    a first bonding member; and
    a second bonding member having a plurality of bonding elements configured to cooperate with the first bonding member to point bond the front region to the back region to define the fin seams, and a slitter disposed outboard of the plurality of bonding elements and configured to simultaneously act on material outboard of the point bonds from both the front and back regions.

11. The bonding and slitting device as set forth in claim 10 wherein the second bonding member has a circumference, the plurality of bonding elements being arranged continuously about the circumference of the second bonding member.

12. The bonding and slitting device as set forth in claim 11 wherein the plurality of bonding elements are aligned in at least two circumferentially extending columns, each column being offset relative to an adjacent column.

13. The bonding and slitting device as set forth in claim 12 wherein each of the columns of bonding elements define a circumferentially extending centerline, each centerline being spaced from an adjacent centerline by a distance between 0.5 mm and 2 mm.

14. The bonding and slitting device as set forth in claim 10 wherein at least some of the plurality of bonding elements are frustum nubs.

15. The bonding and slitting device as set forth in claim 10 wherein the slitter is spaced from the plurality of bonding elements by a distance between 0.5 mm and 5 mm.

16. The bonding and slitting device as set forth in claim 11 wherein slitter extends continuously about a circumference of the second bonding member.

17. The bonding and slitting device as set forth in claim 10 wherein the first bonding member is a rotary ultrasonic horn and the second bonding member is a rotary anvil, the ultrasonic horn and the anvil being configured to counter-rotate with respect to each other.

* * * * *